United States Patent
Ryan et al.

(10) Patent No.: US 11,793,539 B2
(45) Date of Patent: *Oct. 24, 2023

(54) SYSTEMS AND METHODS FOR SUBMUCOSAL TISSUE SEPARATION

(71) Applicant: Boston Scientific Scimed, Inc., Maple Grove, MN (US)

(72) Inventors: Shawn Ryan, Littleton, MA (US); Samuel Raybin, San Jose, CA (US); Matthew B. Hollyer, Watertown, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 363 days.

This patent is subject to a terminal disclaimer.

(21) Appl. No.: 16/952,849

(22) Filed: Nov. 19, 2020

(65) Prior Publication Data

US 2021/0068860 A1    Mar. 11, 2021

Related U.S. Application Data

(63) Continuation of application No. 15/983,968, filed on May 18, 2018, now Pat. No. 10,869,683.

(Continued)

(51) Int. Cl.
*A61B 17/32* (2006.01)
*A61L 31/14* (2006.01)
(Continued)

(52) U.S. Cl.
CPC .......... *A61B 17/320016* (2013.01); *A61B 17/00234* (2013.01); *A61B 17/3478* (2013.01);
(Continued)

(58) Field of Classification Search
CPC ...... A61B 17/320016; A61B 17/00234; A61B 17/3478; A61B 2017/00269;
(Continued)

(56) References Cited

U.S. PATENT DOCUMENTS 6,689,616 B1    2/2004  Bosies et al.
2005/0031540 A1  2/2005  Nielsen
(Continued)

FOREIGN PATENT DOCUMENTS

GB    2302094 A    1/1997
JP    2001192336 A  7/2001
(Continued)

OTHER PUBLICATIONS

International Search Report and Written Opinion dated Oct. 25, 2018 for PCT/US18/33469, 11 pgs.
(Continued)

*Primary Examiner* — George J Ulsh
(74) *Attorney, Agent, or Firm* — Seager, Tufte & Wickhem LLP

(57) ABSTRACT

The present disclosure relates to the field of medical devices generally and specifically, to endoscopic systems and methods for resection of malignant and pre-malignant lesions within the gastrointestinal (GI) tract. In particular, the present disclosure relates to systems and methods for delivering injectable compositions between tissue layers (e.g., between the muscularis and submucosa layers) to elevate and stabilize the lesion for fast and efficient resection.

20 Claims, 4 Drawing Sheets

Related U.S. Application Data

(60) Provisional application No. 62/508,781, filed on May 19, 2017.

(51) Int. Cl.
| | |
|---|---|
| *A61L 31/04* | (2006.01) |
| *A61B 17/00* | (2006.01) |
| *A61M 5/19* | (2006.01) |
| *A61M 5/28* | (2006.01) |
| *A61B 17/34* | (2006.01) |
| *G01R 33/00* | (2006.01) |
| *H01F 27/34* | (2006.01) |
| *A61B 18/14* | (2006.01) |
| *A61B 18/00* | (2006.01) |
| *A61M 5/31* | (2006.01) |
| *A61B 18/08* | (2006.01) |

(52) U.S. Cl.
CPC ........... A61L 31/042 (2013.01); A61L 31/148 (2013.01); A61M 5/19 (2013.01); A61M 5/285 (2013.01); G01R 33/0011 (2013.01); G01R 33/0017 (2013.01); H01F 27/346 (2013.01); *A61B 18/082* (2013.01); *A61B 18/14* (2013.01); *A61B 2017/0034* (2013.01); *A61B 2017/00269* (2013.01); *A61B 2017/00818* (2013.01); *A61B 2017/00942* (2013.01); *A61B 2018/00494* (2013.01); *A61B 2018/00595* (2013.01); *A61B 2018/00601* (2013.01); *A61B 2018/00982* (2013.01); *A61L 2400/06* (2013.01); *A61M 2005/3106* (2013.01)

(58) Field of Classification Search
CPC .. A61B 2017/0034; A61B 2017/00818; A61B 2018/00494; A61B 2018/00595; A61B 2018/00601; A61B 2018/00982; A61L 31/042; A61L 31/148; A61L 2400/06; A61M 5/19; A61M 5/285; A61M 2005/3106

See application file for complete search history.

(56) References Cited

U.S. PATENT DOCUMENTS

| | | |
|---|---|---|
| 2012/0141379 A1 | 6/2012 | Vogel et al. |
| 2014/0187858 A1 | 7/2014 | Adams et al. |
| 2014/0324022 A1 | 10/2014 | Scribben et al. |
| 2017/0165379 A1 | 6/2017 | Wellington |

FOREIGN PATENT DOCUMENTS

| | | |
|---|---|---|
| WO | 2013070692 A1 | 5/2013 |
| WO | 2013169852 A1 | 11/2013 |
| WO | 2015054208 A1 | 4/2015 |

OTHER PUBLICATIONS

International Preliminary Report on Patentability for International Application No. PCT/US2018/033469, dated Nov. 29, 2019, 7 pgs.

SYSTEMS AND METHODS FOR SUBMUCOSAL TISSUE SEPARATION

CROSS REFERENCE TO RELATED APPLICATIONS

This application is a continuation of Ser. No. 15/983,968, filed May 18, 2018, and claims the benefit of priority under 35 U.S.C. § 119 to U.S. Provisional Patent Application Ser. No. 62/508,781, filed on May 19, 2017, which is incorporated by reference in its entirety for all purposes.

FIELD

The present disclosure relates to the field of medical devices generally and specifically, to endoscopic systems and methods for resection of malignant and pre-malignant lesions within the gastrointestinal (GI) tract. In particular, the present disclosure relates to systems and methods for delivering injectable compositions between tissue layers (e.g., between the muscularis and submucosal layers) to separate, elevate and stabilize the lesion for fast and efficient resection.

BACKGROUND

Examples are known of the use of injectable components in medical devices to separate one structure from another in order to either to separate, elevate and/or stabilize the first structure for performing a diagnostic or treatment step safely, fast and efficiently. For example, endoscopic procedures such as endoscopic mucosal resection (EMR), endoscopic submucosal dissection (ESD), colon polypectomy and peroroal endoscopic myotomy (POEM) are commonly performed to detect and remove malignant and pre-malignant lesions, tumors and/or otherwise unhealthy tissues within the mucosal and submucosal layers of the gastrointestinal (GI) tract. To reduce the risk of perforating the GI tract, it is important to separate the submucosal layer from the underlying muscularis layer prior to performing the resection or dissection procedure. A common way to establish this separation is to inject a low viscosity fluid between the muscularis and submucosal tissue layers. However, these low viscosity fluids tend to dissipate within the surrounding tissues and therefore may not sufficiently raise/elevate the submucosal layer for the entire duration of the procedure. While high viscosity fluids may provide the requisite elevation of the submucosal layer, their inability to flow between tissue layers requires high injection forces that tend to damage and/or perforate the tissue layers.

A variety of advantageous medical outcomes may be realized by the systems and/or methods of the present disclosure, which combine the tissue separating capabilities of a low viscosity fluid with the tissue elevating and stabilizing capabilities of a high viscosity fluid.

SUMMARY

The present disclosure, in its various aspects, provides systems and methods for delivering injectable compositions between tissue layers (e.g., between the muscularis and submucosal layers) to separate, elevate and stabilize the tissue layers for efficient visualization and/or resection. The injectable compositions disclosed herein may be introduced between any two adjacent tissue or muscle layers that require separating and in areas of the body outside of the GI tract (e.g., uterus, bladder, etc.).

In one aspect, the present disclosure relates to a system, comprising a delivery device that includes a proximal portion, a distal portion and a lumen extending therebetween. A first injectable composition may be disposed within a distal portion of the delivery device, and a second injectable composition may be disposed within a proximal portion of the delivery device. A viscosity of the first injectable composition may be less than a viscosity of the second injectable composition. For example, a viscosity of the second injectable composition may be at least ten times greater than a viscosity of the first injectable composition. The first and second injectable compositions may not substantially mix within the lumen of the delivery device. The first and second injectable compositions may be separated by a barrier member. The barrier member may be configured to rupture above a threshold level of force. The barrier member may include a biocompatible or biodegradable material. The second injectable composition may include a hydrophilic polymer including, by way of non-limiting example, acrylate-based polymers, polyurethane-based polymers, polynorbornene-based polymer and polylactide-based polymers. The hydrophilic polymer may include a polysaccharide, including, by way of non-limiting example, a xanthan gum. The delivery device may include a sharpened distal end. The delivery device may be delivered through a working channel of a scope, sheath or catheter-based instrument, among other examples, including, by way of non-limiting example, an endoscope or colonoscope.

In another aspect, the present disclosure relates to a system, comprising a first delivery device loaded with a first injectable composition, and a second delivery device loaded with a second injectable composition. A viscosity of the first injectable composition may be less than a viscosity of the second injectable composition. For example, a viscosity of the second injectable composition may be at least ten times greater than a viscosity of the first injectable composition. The second injectable composition may include a hydrophilic polymer including, by way of non-limiting example, acrylate-based polymers, polyurethane-based polymers, polynorbornene-based polymer and polylactide-based polymers. The hydrophilic polymer may include a polysaccharide including, by way of non-limiting example, a xanthan gum. The first and/or second delivery devices may include a sharpened distal end. The first and/or second delivery devices may be delivered through a working channel of a scope, including, by way of non-limiting example, an endoscope or colonoscope.

In another aspect, the present disclosure relates to a method for resecting tissue, comprising positioning a portion of a delivery device between adjacent first and second tissue layers, delivering a first injectable composition through a lumen of the delivery device into a region between the adjacent first and second tissue layers such that at least a portion of the first and second tissue layers are separated, delivering a second injectable composition through the lumen of the delivery device into the separation between the first and second tissue layers created by the first injectable composition and resecting at least a portion of the first tissue layer. The delivery device may include a proximal portion, distal portion and lumen extending therebetween. A viscosity of the first injectable composition may be less than a viscosity of the second injectable composition. The second injectable composition may raise or elevate the first tissue layer above the second tissue layer. The first tissue layer may include a submucosal tissue layer. The second tissue layer may include a muscularis tissue layer. The submucosal tissue layer may include a lesion.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of ordinary skill in the art to understand the disclosure. In the figures.

Figure 1:
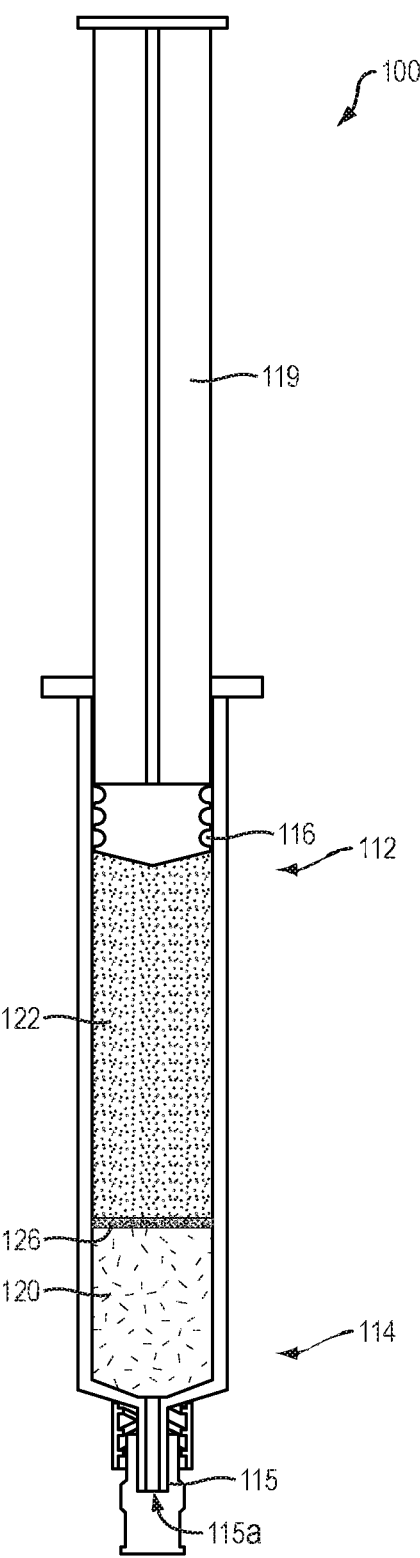
FIG. 1 provides a perspective view of a delivery device filled with injectable compositions, according to one embodiment of the present disclosure.

It is noted that the drawings are only intended to depict typical or exemplary embodiments of the disclosure. It is further noted that the drawings may not be necessarily to scale. Accordingly, the drawings should not be considered as limiting the scope of the disclosure. The disclosure will now be described in greater detail with reference to the accompanying drawings.

DETAILED DESCRIPTION

Before the present disclosure is described in further detail, it is to be understood that the disclosure is not limited to the particular embodiments described, as such may vary. It is also to be understood that the terminology used herein is for the purpose of describing particular embodiments only, and is not intended to be limiting beyond the scope of the appended claims. Unless defined otherwise, all technical terms used herein have the same meaning as commonly understood by one of ordinary skill in the art to which the disclosure belongs. Finally, although embodiments of the present disclosure are described with specific reference to the use of an endoscope to deliver injectable compositions between tissue layers of the GI tract (e.g., between the muscularis and submucosa layers) to separate and elevate the tissue layers for efficient visualization and/or resection, it should be appreciated that such injectable compositions may be delivered using a variety of delivery systems (e.g., guide lumens, catheters, ports, and the like) that are inserted into a variety of lumens of a patient.

As used herein, the term "injectable composition" includes any sterile, flowable and biologically inert fluid that may be introduced between the tissue layers of a patient. In various embodiments, the injectable compositions may comprise a suitable hydrophilic polymer mixed or dissolved in an aqueous solution. For example, the hydrophilic polymer may include a polysaccharide (e.g., xanthum gum, gellan gum, chitosan, cellulose, amylose, pectin, alginates, hyaluronic acid and salts or derivatives thereof) dissolved in normal isotonic saline. Polysaccharides for use in conjunction with the present disclosure may vary widely in molecular weight, ranging, for example, from 5 kDa or less to 20,000 kDa or more. The viscosity of these injectable compositions may be varied, depending on the specific requirements of a medical procedure, by increasing or decreasing the concentration of the polysaccharide. As discussed in greater detail below, the injectable compositions of the present disclosure may be provided in, and delivered from, a syringe, needle or other suitable delivery device.

As used herein, the term "viscosity" relates to the degree to which a fluid resists flow under an applied force. Addition of a given polysaccharide to an aqueous solution results in an increase in viscosity of that solution. Solution viscosity is a function of both the polymer concentration and the molecular weight of the polymer. At a given constant weight concentration, solution viscosity typically exhibits an exponential relationship with the molecular weight of the polymer used to adjust the viscosity of the solution. Consequently, an increase in molecular weight for a given polymer will allow a lower concentration (by weight) of the polymer to be used to achieve a given viscosity, whereas a decrease in molecular weight for a given polymer will allow a higher concentration (by weight) of the polymer to be used to achieve a given viscosity.

As used herein, the term "distal" refers to the end farthest away from a medical professional when introducing a device into a patient, while the term "proximal" refers to the end closest to the medical professional when introducing a device into a patient.

As used herein, the term "resection," dissection" and grammatical equivalents thereof, includes the removal of a tissue lesion and/or tumor from surrounding healthy tissue using a variety of tissue cutting techniques known in the art. By way of non-limiting example, such cutting techniques may include electrocautery-based tissue cutting elements and/or tissue cutting elements that include sharpened surfaces (i.e., knives, scalpels, scissors, and the like).

The present disclosure in various embodiments relates generally to systems and methods for separating and lifting the submucosal tissue layer from the underlying muscularis layer for safe and efficient visualization and/or resection of a tissue lesion. In one embodiment, a tissue resection procedure of the present disclosure may include the following steps: 1) positioning an endoscope within a lumen of a patient adjacent to a known or suspected tissue lesion, 2) advancing a delivery device through a working channel of the endoscope such that a sharpened distal end of the delivery device penetrates a tissue wall of the lumen and is positioned between the muscularis and submucosal layers, 3) delivering a first (e.g., low viscosity) injectable composition between the muscularis and submucosal tissue layers to separate the tissue layers, 4) delivering a second (e.g., high viscosity) fluid into the space created by the first injectable composition to elevate (e.g., lift) the submucosal layer from the underlying muscularis layer and 5) resecting the tissue lesion using a tissue cutting element disposed within a working channel of the endoscope.

Referring to FIG. 1, in one embodiment, an injectable composition delivery device 100 of the present disclosure may include a proximal portion 112, a distal portion 114 and a lumen 116 extending therebetween. The distal portion 114 of the delivery device 100 may be filled with a first (e.g., low viscosity) injectable composition 120, and the proximal portion 112 of the delivery device 100 may be filled with a second (e.g., high viscosity) injectable composition 122. In various embodiments, the first injectable composition may include a range of viscosities (e.g., a viscosity of approximately 0.0 centipoise (cP) to a viscosity of approximately 10.0 cP or more). Similarly, the second injectable composition may include a range of viscosities approximately ten times greater (e.g., approximately 100.0 cP) than the viscosity of the first injectable composition. The high viscosity second injectable composition 122 may include, by way of non-limiting example, a gellan gum, or other substance, which forms a pseudosolid gel at room temperature. In one embodiment, a gellan gum may be mixed at room temperature with an aqueous isotonic solution (e.g., normal saline, etc.) to a final concentration of approximately 0.10%, and dissolved by heating the solution to approximately 70° C. Upon cooling to approximately 40° C., the solution may solidify into a brittle injectable gel that resists mixing with the first (e.g., low viscosity) injectable composition. In one embodiment, the first injectable composition 120 may include a lower concentration of the gellan gum of the second injectable composition, dissolved in the same or different aqueous isotonic solution. Alternatively, the first injectable composition may not include any amount (e.g., 0.0%) of the gellan gum. A plunger 119 may be slidably disposed within the lumen 116 of the delivery device 100 to sequentially deliver the first and second injectable compositions 120, 122 through an opening 115a on the distal end 115 of the delivery device 100 as the plunger 119 is advanced distally. In one embodiment, the semi-solid nature of the second injectable composition 122 may prevent mixing of the first and second injectable compositions as the plunger is distally advanced. In addition, or alternatively, the first and second injectable compositions 120, 122 may be separated by a barrier member 126. In one embodiment, the barrier member may be formed from a destructible membrane configured to rupture after the first injectable composition 120 has been discharged from the distal portion 114 of the delivery device 100. By way of non-limiting example, the barrier member 126 may be formed from a high concentration of gellan gum, or other suitable biocompatible and/or biodegradable material, as are known in the art.

Although FIG. 1 depicts a delivery device 100 that includes unequal volumes of the first and second injectable compositions 120, 122, in various embodiments, the relative amounts (e.g., volumes) of the first and second injectable compositions 120, 122 may vary. In addition, or alternatively, the delivery device 100 may include different arrangements of the first and second injectable compositions 120, 122. For example, the delivery device 100 may be loaded with two or more portions of the second injectable composition 122, each of which may be separated by a separate portion of the first injectable composition 120 and/or a barrier member 126. Such an alternating arrangement of the first and second injectable compositions 120, 122 may allow a medical professional to resect or dissect multiple tissue lesions in succession and/or sequentially resect separate portions of a single large lesion, as discussed below. In addition, or alternatively, the systems and methods of the present disclosure are not limited to only first and second injectable compositions with different viscosities, but may include any number of injectable compositions with a range of different viscosities. In various embodiments, the devices and methods of the present disclosure are not limited to injectable compositions loaded within a single delivery device, but may include two or more delivery devices (e.g., arranged in tandem, or as separate delivery devices) with each delivery device loaded with a different one of the injectable compositions.

Figure 2A:
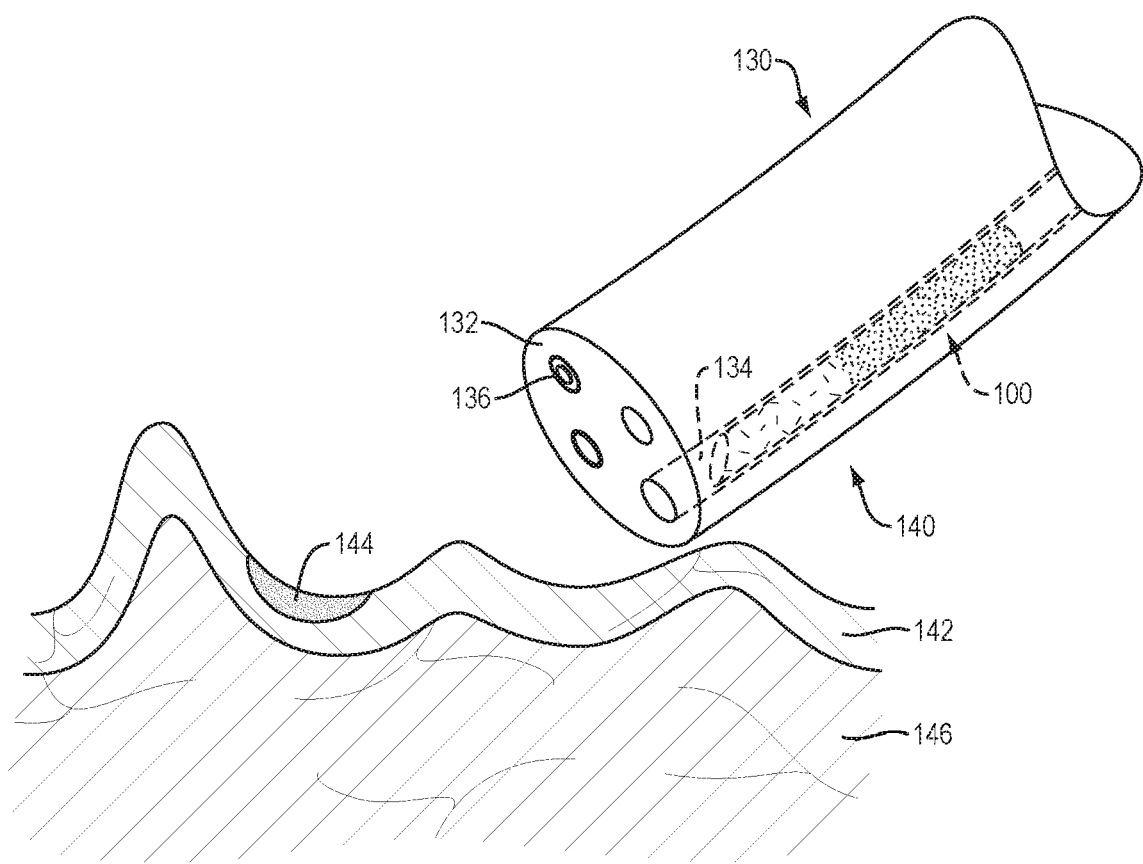
FIGS. 2A-2D illustrate representative steps of a submucosal tissue resection procedure, according to one embodiment of the present disclosure.

Referring to FIG. 2A, in use and by way of example, an endoscope 130 may be positioned within the lumen 140 of the GI tract adjacent to a known or suspected tissue lesion 144 within the submucosal layer 142. The endoscope 130 may include a distal end 132, a proximal end (not shown) and a working channel 134 extending therebetween. The distal end 132 of the endoscope 130 may include a camera 136 to visualize the working area and assist the medical professional in navigating the tortuous anatomy of the GI tract. A variety of extendable/retractable medical instruments, including, for example, the delivery device 100 and/or a tissue cutting element 138 (e.g., FIG. 2D) may extend through the working channel 134 to manipulate tissues beyond the distal end of the endoscope. As evidenced by the proximity of the tissue lesion 144 to the muscularis layer 146, resection of the tissue lesion 144 without lifting and separating the submucosal layer 142 from the underlying muscularis layer 146 would be technically challenging, time consuming and present a high likelihood of perforating the muscularis layer.

Figure 2B:
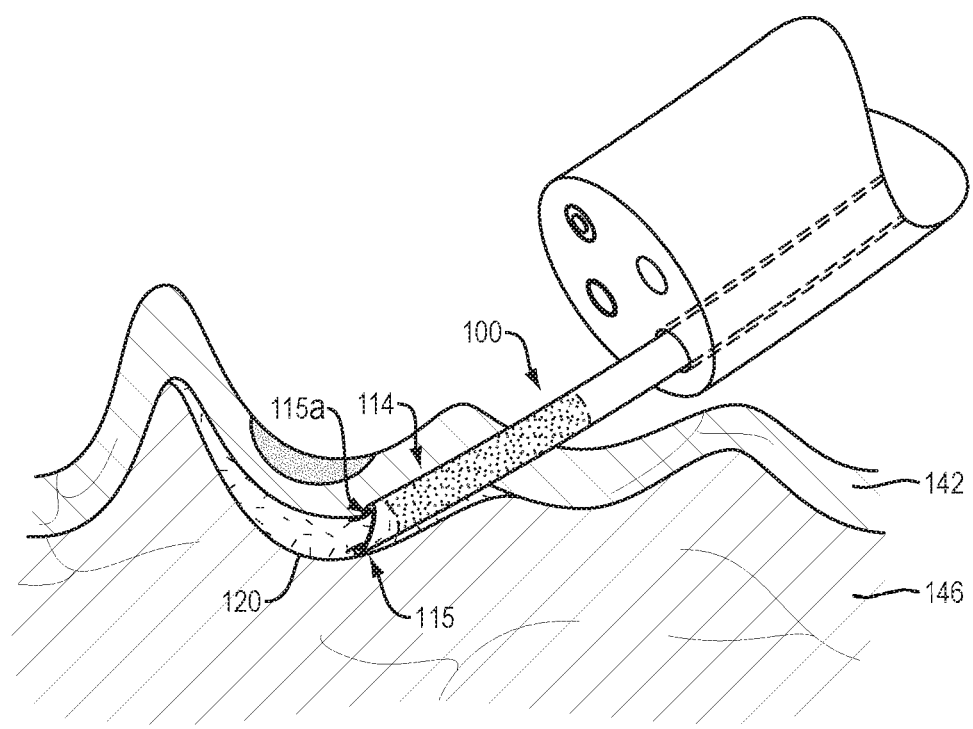

Referring to FIG. 2B, the distal end 115 of the delivery device 100 may include a sharpened end configured to penetrate the submucosal layer 142 and position an opening 115a of the delivery device 100 between the submucosal and muscularis tissue layers 142, 146. The first injectable composition 120 may then be advanced through the distal portion 114 of the delivery device 100 to flow between and separate the submucosal layer 142 from the underlying muscularis layer 146. In various embodiments, the amount (e.g., volume) of the first injectable composition 120 delivered between the tissue layers may be varied depending on the size, shape and/or location of the tissue lesion.

Figure 2C:
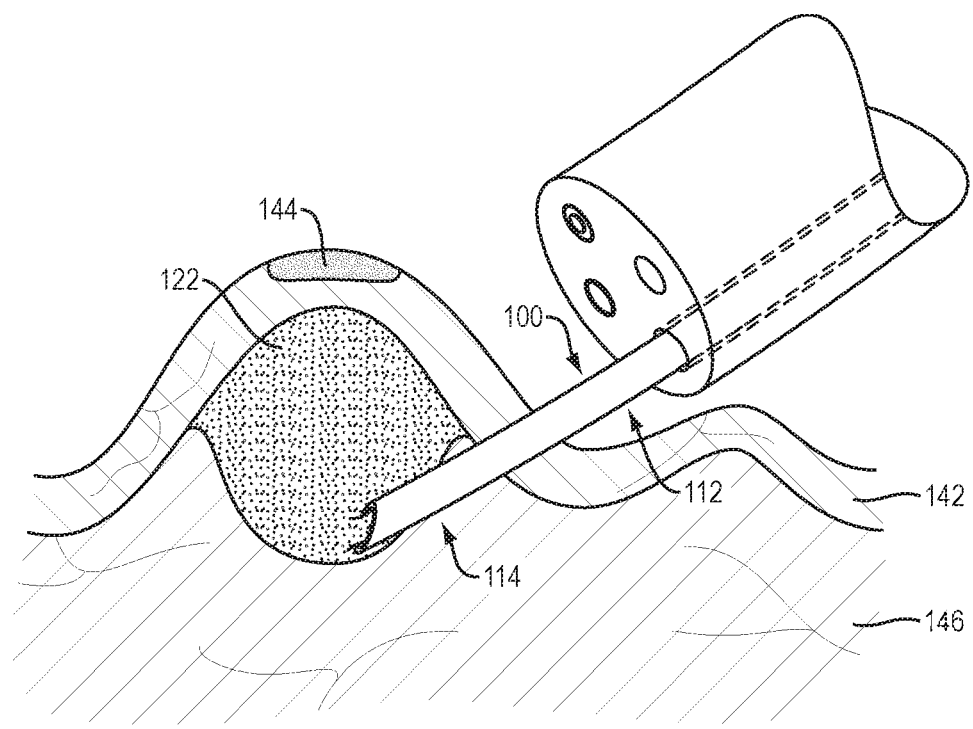

Referring to FIG. 2C, with the submucosal and muscularis tissue layers 142, 146 sufficiently separated, the second injectable composition 122 may be advanced through the proximal and distal portions 112, 114 of the delivery device 100 into the space created by the first injectable composition. Because the submucosal and muscularis tissue layers 142, 146 are already separated by the first injectable composition, the second injectable composition 122 may be delivered between the tissue layers with significantly reduced force, thereby minimizing the potential for tissue trauma and/or perforation. In addition, the inability of the second injectable composition 122 to flow into or between the non-separated portions of the submucosal and muscularis tissue layers 142, 146 may provide an outward radial force which elevates the submucosal layer 142 (and tissue lesion 144 therein) from the underlying muscularis layer 146 to form a protrusion or "bleb." As above, the amount (e.g., volume) and/or viscosity of the second injectable composition 122 may vary depending on the size, shape and/or location of the tissue lesion.

Figure 2D:
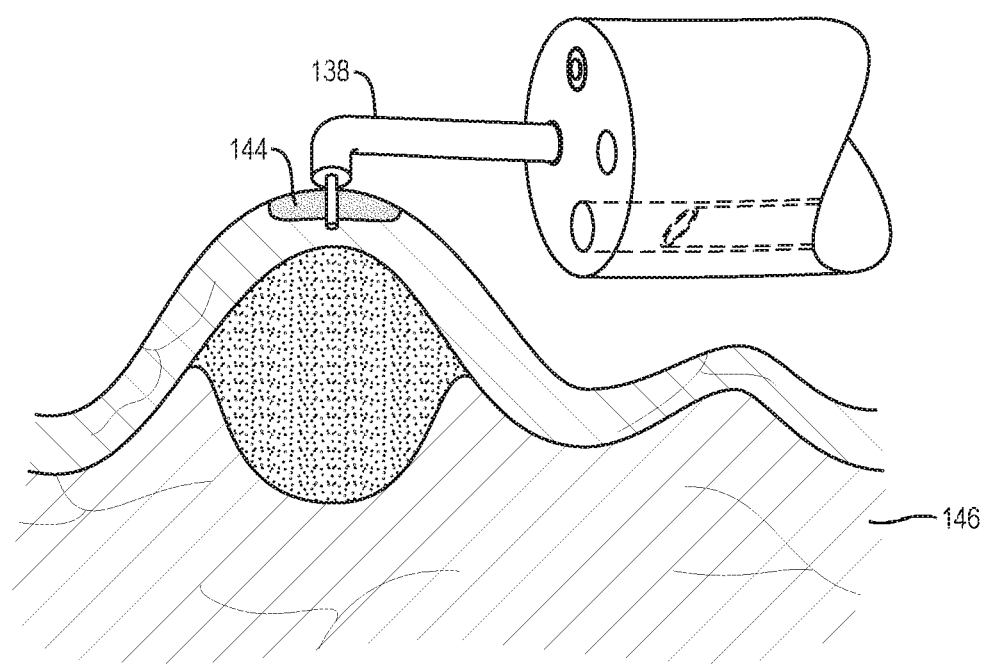

Referring to FIG. 2D, a tissue cutting element 138 may then be deployed through a working channel of the endoscope to resect the tissue lesion 144 along its margins. In various embodiments, the protrusion or "bleb" may improve the medical professional's ability to visualize the tissue lesion 144 and/or provide a space or buffer zone to minimize the likelihood of accidentally cutting into the muscularis layer 146. In addition, the radial force exerted by the second injectable composition may also place the tissue lesion 144 and surrounding healthy tissue under constant and consistent pressure to minimize movement of (e.g., immobilize) the tissue lesion 144 and/or provide a firm surface against which tissue cutting element 138 may exert force for precise resection along the margins of the tissue lesion. Alternatively, in situations in which the tissue lesion may extend into (e.g., invades) the muscularis layer 146, the medical professional may visualize the inability of the tissue layers to be separated by the second injectable composition, thereby identifying a lesion that is not amenable to a standard resection procedure.

While embodiments of the present disclosure are described with reference to endoscopic procedures performed within the GI tract, e.g., endoscopic mucosal resection (EMR) or endoscopic submucosal dissection (ESD), embodiments of the present disclosure may be used for other suitable endoscopic procedures, or for procedures other than the endoscopic procedures, such as urologic procedures, plastic surgeries or open invasive surgeries. In addition, embodiments of the disclosure may be applied to numerous portions of a body, other than the GI tract.

All of the systems and/or methods disclosed and claimed herein can be made and executed without undue experimentation in light of the present disclosure. While the systems and methods of this disclosure have been described in terms of preferred embodiments, it may be apparent to those of skill in the art that variations may be applied to the systems and/or methods and the steps or sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A system, comprising:
    a delivery device comprising a proximal portion, distal portion and lumen extending therebetween;
    a first injectable composition disposed within the distal portion of the delivery device;
    and a second injectable composition disposed within the proximal portion of the delivery device;
    wherein a viscosity of the first injectable composition is less than a viscosity of the second injectable composition;
    wherein the first and second injectable compositions are separated by a barrier member;
    and wherein the system is configured to sequentially deliver the first and second injectable compositions.

2. The system of claim 1, wherein the barrier member is configured to rupture above a threshold level of force.

3. The system of claim 1, wherein the barrier member includes a biocompatible or biodegradable material.

4. The system of claim 1, wherein the second injectable composition comprises a hydrophilic polymer selected from the group consisting of acrylate-based polymers, polyurethane-based polymers, polynorbornene-based polymer and polylactide-based polymers.

5. The system of claim 4, wherein the hydrophilic polymer further comprises a polysaccharide.

6. The system of claim 5, wherein the polysaccharide is a xanthan gum.

7. The system of claim 1, wherein the delivery device includes a sharpened distal end.

8. The system of claim 1, wherein the delivery device is configured to be delivered through a working channel of an endoscope.

9. A system, comprising:
    a delivery device comprising a proximal portion, distal portion and lumen extending therebetween;
    a first injectable composition disposed within the distal portion of the delivery device;
    and a second injectable composition disposed within the proximal portion of the delivery device;
    wherein a viscosity of the first injectable composition is less than a viscosity of the second injectable composition;
    wherein the first and second injectable compositions are separated by a barrier member;
    wherein the delivery device is configured to (a) extend through a working channel of an endoscope that comprises a proximal end, a distal end and said working channel such that a distal end of the delivery device extends into tissue beyond the distal end of the endoscope and such that the distal end of the delivery device is positioned between adjacent first and second tissue layers and (b) inject the first and second injectable compositions between the first and second layers; and
    wherein the system is configured to sequentially deliver the first and second injectable compositions.

10. The system of claim 9, wherein the barrier member is configured to rupture above a threshold level of force.

11. The system of claim 9, wherein the barrier member includes a biocompatible or biodegradable material.

12. The system of claim 9, wherein the viscosity of the second injectable composition is at least ten times greater than the viscosity of the first injectable composition.

13. The system of claim 9, wherein the second injectable composition comprises a hydrophilic polymer selected from the group consisting of acrylate-based polymers, polyurethane-based polymers, polynorbornene-based polymer and polylactide-based polymers.

14. The system of claim 13, wherein the hydrophilic polymer further comprises a polysaccharide.

15. The system of claim 14, wherein the polysaccharide is a xanthan gum.

16. The system of claim 9, wherein the delivery device includes a sharpened distal end.

17. A system, comprising:
    a delivery device comprising a proximal portion, distal portion and lumen extending therebetween;
    a first injectable composition disposed within the distal portion of the delivery device;
    and a second injectable composition disposed within the proximal portion of the delivery device;
    wherein the viscosity of the second injectable composition is at least ten times greater than the viscosity of the first injectable composition;
    wherein the first and second injectable compositions are separated by a barrier member;
    and wherein the system is configured to sequentially deliver the first and second injectable compositions.

18. The system of claim 17, wherein the barrier member is configured to rupture above a threshold level of force.

19. The system of claim 17, wherein the second injectable composition comprises a hydrophilic polymer selected from the group consisting of acrylate-based polymers, polyurethane-based polymers, polynorbornene-based polymer and polylactide-based polymers.

20. The system of claim 17, wherein the delivery device is configured to be delivered through a working channel of an endoscope.

* * * * *